United States Patent
Rothämel et al.

(10) Patent No.: US 7,655,825 B2
(45) Date of Patent: Feb. 2, 2010

(54) METHOD FOR THE PRODUCTION OF SYNTHETIC FUELS FROM OXYGENATES

(75) Inventors: Martin Rothämel, Frankfurt-Niedererlenbach (DE); Bernd Ahlers, Dietzenbach (DE); Matthias Wagner, Nidderau (DE); Harold Koempel, Neu-Isenburg (DE); Juergen Hofmockel, Frankfurt am Main (DE)

(73) Assignee: Lurgi AG, Frankfurt am Main (DE)

( * ) Notice: Subject to any disclaimer, the term of this patent is extended or adjusted under 35 U.S.C. 154(b) by 0 days.

(21) Appl. No.: 11/795,930

(22) PCT Filed: Dec. 1, 2005

(86) PCT No.: PCT/EP2005/012789

§ 371 (c)(1),
(2), (4) Date: Mar. 24, 2008

(87) PCT Pub. No.: WO2006/076942

PCT Pub. Date: Jul. 27, 2006

(65) Prior Publication Data

US 2009/0050531 A1 Feb. 26, 2009

(30) Foreign Application Priority Data

Jan. 22, 2005 (DE) ...................... 10 2005 003 109

(51) Int. Cl.
*C10G 35/95* (2006.01)

(52) U.S. Cl. ................ 585/639; 585/315; 585/316; 585/324; 585/329; 585/330; 585/640; 208/141

(58) Field of Classification Search ................ 208/141; 585/315–316, 324, 639–640, 329–330
See application file for complete search history.

(56) References Cited

U.S. PATENT DOCUMENTS

| | | | | |
|---|---|---|---|---|
| 4,456,779 A | * | 6/1984 | Owen et al. .................. | 585/415 |
| 4,579,999 A | * | 4/1986 | Gould et al. ................. | 585/312 |
| 4,616,098 A | * | 10/1986 | Hoelderich et al. ......... | 585/640 |
| 4,689,205 A | | 8/1987 | Gould | |
| 4,851,606 A | * | 7/1989 | Ragonese et al. ........... | 585/640 |
| 5,063,187 A | | 11/1991 | Burgfels ....................... | 502/71 |
| 5,672,800 A | | 9/1997 | Mathys et al. | |
| 7,015,369 B2 | | 3/2006 | Hack ........................... | 585/640 |

* cited by examiner

*Primary Examiner*—Robert J Hill, Jr.
*Assistant Examiner*—Brian McCaig
(74) *Attorney, Agent, or Firm*—Jonathan Myers; Andrew Wilford

(57) ABSTRACT

A method is disclosed for producing a synthetic fuel, especially diesel fuel and in addition gasoline, liquefied petroleum gas and heating gas from a gas mixture comprising an oxygenate wherein the oxygenate is methanol and/or dimethyl ether and/or another oxygenate, through a series of steps, including olefin-formation, oligomerization of the olefins, and several separation steps and recycling steps, in particular the recycling of a stream of saturated hydrocarbons following the oligomerization of olefins back to the olefin-forming stage, to obtain the diesel fuel and the other synthetic fuels in high yield.

10 Claims, 1 Drawing Sheet

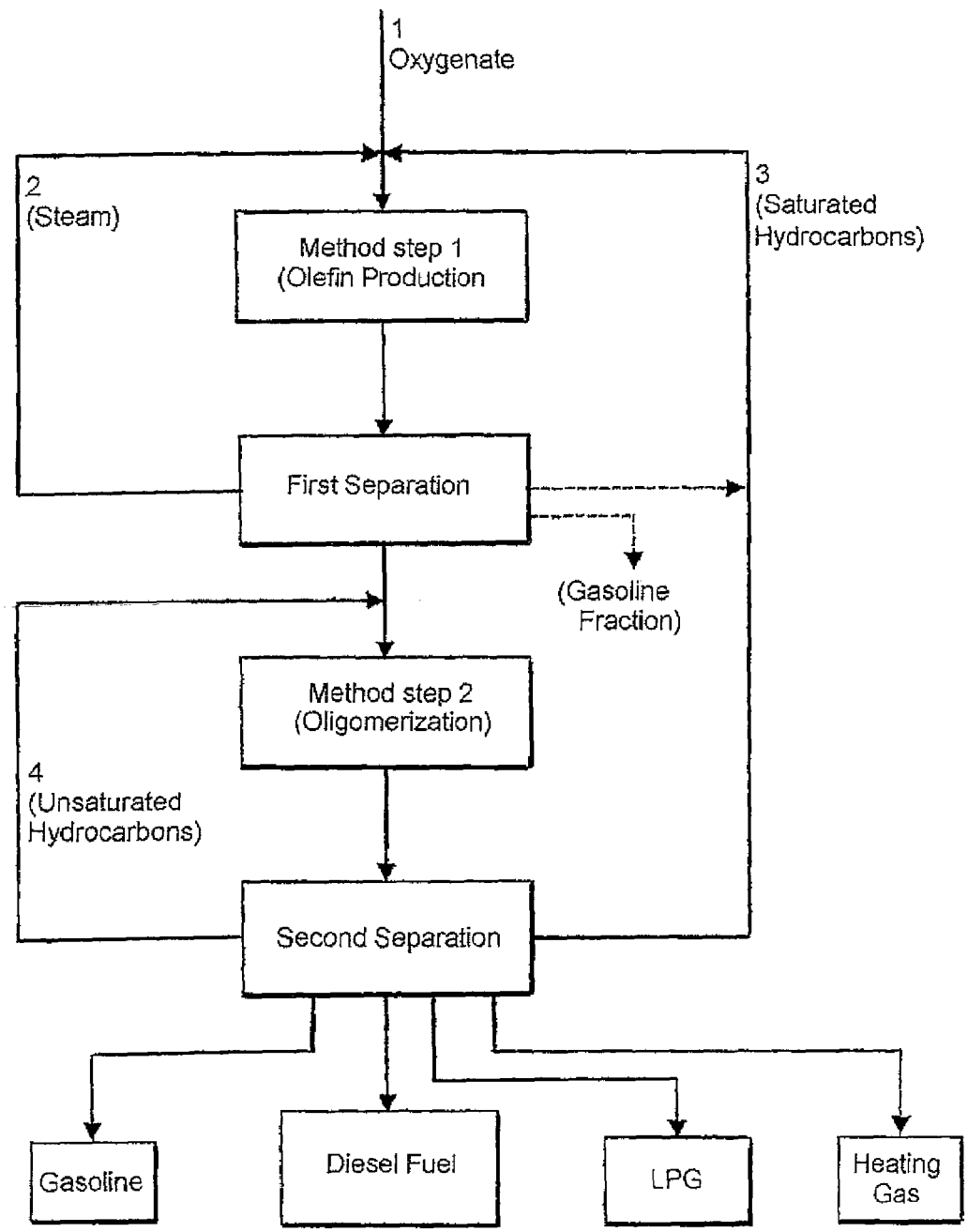

METHOD FOR THE PRODUCTION OF SYNTHETIC FUELS FROM OXYGENATES

CROSS REFERENCE TO RELATED APPLICATIONS

This application is the U.S. national phase of PCT application PCT/EP2005/012789, filed 1 Dec. 2005, published 27 Jul. 2006 as WO 2006/076942, and claiming the priority of German patent application 102005003109.9 itself filed 22 Jan. 2005, whose entire disclosures are herewith incorporated by reference.

The invention relates to a multistep method for producing synthetic fuels from oxygenates such as methanol and/or dimethyl ether in order to optimize the yield of diesel fuel. Synthetic fuels are understood to mean diesel fuel, kerojet fuel, and gasoline.

BACKGROUND OF THE INVENTION

Several methods for producing synthetic fuels have previously been developed. In particular, methods are known for the production of synthetic fuels from methanol.

In principle, these methods may be divided into two steps. In the first method step (olefin production), oxygenates are reacted to form preferably $C_2$-$C_8$ olefins, using a zeolite catalyst. In a second method step (oligomerization), the referenced olefins are converted to higher hydrocarbons at elevated pressure, using a zeolite catalyst. Between the two method steps, substreams composed of water and/or hydrocarbon may be separated out in a first separation step. After the second method step, in a second separation the higher hydrocarbons obtained are separated into a light fraction, a gasoline fraction, and a heavy fraction. After hydrogenation, the heavy fraction forms the diesel fuel end product, and with suitable separation, kerojet fuel as well. The liquefied petroleum gas (LPG) and heating gas products may be obtained from the light fraction.

The known methods considered below represent substeps of the above-described overall method.

The first method step (olefin production) is described, for example, in the production of in particular propylene from methanol in European patents EP 0 448 000 B1 and EP 0 882 692 B1 and in German patent applications DE 100 27 159 [U.S. Pat. No. 7,015,369] and DE 101 17 248 [Also U.S. Pat. No. 7,015,369]. The methanol to propylene (MTP) process, which employs a multistage fixed-bed reactor, is used in this method, and a pentasil-type zeolite is used as catalyst. To optimize product yield, a gas stream rich in unsaturated hydrocarbons is recirculated to the olefin reactor, and in this method step is separated from the reactor product. In addition, a portion of the water produced in the olefin production is recirculated. In the MTP process, however, the product sought in this method step is propylene, not olefins, for example.

The principle of the first method step (olefin production) is used in other patents for the production of gasoline. Cited here are U.S. Pat. Nos. 4,404,414, 4,788,369, and 4,035,430. The methods described therein are also carried out using multistage fixed-bed reactors loaded with zeolite catalyst (ZSM 4 or similar catalysts). Here as well, gas streams composed of saturated and unsaturated hydrocarbons (depending on the patent) are recirculated to the reactor. The purpose of recirculation is to adjust the temperature profile in the reactor and optimize the product yield of gasoline. However, unlike the previously referenced MTP process, in these patents no water is used as a recirculation stream.

The second method step (oligomerization), in which higher hydrocarbons are oligomerized from olefins and may then be hydrogenated to produce diesel fuel, is known from South African patents 9,101,969, 9,101,970, and 9,200,642. In this case, catalysts based on crystalline aluminum silicates of the pentasil type, in particular as described in European Patent 369 364 [U.S. Pat. No. 5,063,187], are used for the oligomerization. A multistage fixed-bed reactor is used here as well. This method is used primarily for producing diesel fuel from hydrocarbons which preferably contain $C_2$ to $C_8$ olefins. Also in this method, a recirculation stream is used for optimizing the product yield.

In addition, the combination of a method for producing olefins from methanol with a method for producing gasoline and diesel fuel from olefins is the subject matter of several patents.

In this regard, reference is made in particular to U.S. Pat. Nos. 4,579,999, 4,689,205, and 4,898,717. The cited patents describe a two-step process for producing diesel fuel and gasoline from methanol. The methanol to olefins (MTO) process is used in combination with the MOGD (Mobil olefins to gasoline/distillate) process for the oligomerization of olefins. All three patents use zeolite-type catalysts, and describe the preferred operating conditions for producing diesel fuel.

In the first two U.S. Pat. Nos. 4,689,205 and 4,898,717 [sic; U.S. Pat. No. 4,579,999], a fluidized bed reactor is used in the first method step. In addition, a substream from the gasoline product in the form of an unsaturated hydrocarbon stream is recycled to the first and second method steps. Ethylene and ethane are additionally recycled to the first method step.

In the third U.S. Pat. No. 4,898,717 a multistage fixed-bed reactor is used in both method steps. In this case, the first method step is carried out without recirculation. From the MTO reactor product of the first method step a $C_2$ stream is separated as a by-product from which ethylene is obtained. This is meaningful in this process, since under the described operating conditions approximately 26% by weight of the MTO reactor product is composed of ethylene. This obviously reduces the overall conversion of methanol to diesel fuel.

The MTP process as well as the MTO process using a fluidized bed reactor are both characterized in that in the first method step the olefin production is carried out in the presence of a gas stream that is enriched with unsaturated hydrocarbons separated from the product stream of the first or second method step and returned to the first method step. The yield of propylene is thus optimized in the MTP process. In the MTO-MOGD process, unsaturated hydrocarbons are recirculated from the gasoline by-product, thereby increasing the product yield of diesel fuel and reducing the product yield of gasoline.

However, as a result of the recirculation of olefin-rich streams to the olefin reactor the olefins are partially converted into paraffins and other components. Paraffins and other components are no longer available in the oligomerization reactor for the formation of long-chain hydrocarbons, which in the end reduces the yield of diesel fuel.

DESCRIPTION OF THE METHOD ACCORDING TO THE INVENTION

The object of the method according to the invention is to develop a method for producing synthetic fuels from methanol and/or dimethyl ether and/or another oxygenate, in which the yield of diesel fuel is greatly increased.

This object is achieved by a method for producing synthetic fuels in which in a first method step a gas mixture composed of, for example, methanol and/or dimethyl ether in addition to steam is reacted at temperatures between 300 and 600° C. to form olefins preferably containing 2 to 8 carbon atoms, and in a second method step the olefin mixture obtained is oligomerized at elevated pressure to form higher olefins predominantly containing more than 5, preferably 10 to 20, carbon atoms.

According to the invention, in the first method step olefins are produced in the presence of a gas stream composed essentially of saturated hydrocarbons, which are separated from the product stream of the second method step and returned to the first method step. In a second method step the olefin production is then carried out in the presence of a steam stream which is separated from the product stream of the first method step and returned to the first method step.

This approach is based on the discovery that the product yield of diesel fuel is greatly increased by the recirculation of a gas stream composed predominantly of saturated hydrocarbons as well as by the recirculation of water to the first method step.

The recirculation of water to the first method step reduces coking of the catalyst. Both recirculation streams to the first method step, i.e. water and hydrocarbons, reduce the partial pressure of the reactive components and reduce the adiabatic temperature increase in the reactor, thereby improving the selectivity of the catalyst with regard to the desired products.

The hydrocarbon stream recirculated to the first method step is composed predominantly of saturated hydrocarbons containing 2 to 8 carbon atoms, preferably 3 to 5 carbon atoms, and in the separation after the second method step is removed from the reactor product of the second method step.

The recirculated water stream is composed of a substream of reaction water that in the separation after the first method step is removed from the reactor product of the first method step. In addition, a light fraction containing less than 3 carbon atoms may be separated from the product of the first method step and at least partially recycled to the feed stream for the first method step. Furthermore, in principle it is possible to separate a gasoline fraction after the first method step. However, this would reduce the yield of diesel fuel.

The olefins contained in the reaction product of the first method step are largely converted to higher hydrocarbons through oligomerization in the second method step.

In the subsequent separation two hydrocarbon streams are prepared, of which the first is preferably composed of saturated hydrocarbons and is recirculated to the first method step. The second hydrocarbon stream differs in composition from the first hydrocarbon stream, and is recirculated to the second method step. In addition, the products diesel fuel, gasoline, LPG, and heating gas are separated, diesel fuel being obtained from the heavy fraction of the reactor product through hydrogenation.

Both the olefin reactor and the oligomerization reactor are designed as multistage adiabatic fixed-bed reactors, different designs of the reactors being possible such as layered reactors, radial reactors, tubular reactors, and others. In this method, a pentasil-type zeolite catalyst is preferably used for both the olefin production and the oligomerization. This catalyst preferably has an Si/Al atomic ratio of greater than 10, a BET surface of 300 to 600 m$^2$/g, and a pore volume of 0.3 to 0.8 cm$^3$/g, determined by mercury porosimetry. In a departure from the aluminum silicate type of catalyst mentioned here, catalysts based on silicalite material or aluminum phosphate (SAPO type) may also be used. In addition, the catalyst may be present either in the form of extrudates or in the form of a zeolite-coated ceramic substrate.

The method according to the invention is carried out in the first method step at a temperature between 300° C. and 600° C., preferably between 400° C. and 500° C., particularly preferably between 450° C. and 480° C., and at a pressure of 0 to 12 bar, preferably 1 to 5 bar, particularly preferably 1 to 2 bar.

The remaining reaction product of the first method step is supplied to the second method step for oligomerization. Oligomerization of the olefins substantially removes $C_3$ to $C_5$ olefins from the reaction product of the second method step. Therefore, when a short-chain hydrocarbon stream ($C_9$ and shorter, preferably $C_5$ and shorter) separated from the reactor product of the oligomerization reactor is recirculated, only small quantities of olefins are returned to the first method step. In this manner loss of olefins, which would also result in reduced yield of synthetic diesel fuel in the second method step, is largely avoided.

In contrast to the recirculation of saturated hydrocarbons to the olefin reactor, the yield from the oligomerization reactor may be optimized by recirculating unsaturated hydrocarbons. The quality of the fuel is primarily influenced by adjustment of the olefin/paraffin ratio in the gas stream supplied to the oligomerization process. The characteristics of the synthetic fuel thus produced may be influenced substantially by regulating this mixing ratio.

FIG. 1 shows a schematic overview of the most important steps of the method according to the invention:

The methanol used for fuel production is evaporated, and dimethyl ether is optionally produced from a portion thereof. After introduction of steam 2 and a gas stream 3 preferably containing light paraffins, this gas mixture 1 is reacted in the first method step (olefin production) at temperatures of 300 to 600° C., preferably 450 to 480° C., and a pressure of 0 to 12 bar, preferably 1 to 2 bar, in the presence of pentasil-type zeolite catalysts to form an olefin mixture. The olefins thus obtained preferably contain 2 to 9 carbon atoms. The water produced in the first method step is separated from the reactor product, and a portion thereof is recirculated. A light fraction ($C_2$) may then be separated for yield optimization, and a portion thereof may be recirculated to the first method step. It is particularly advantageous when the molar ratio of the saturated hydrocarbons in the recycle stream 3 to the oxygenates in the feed stream 1 is between 0.5 and 10.

The remaining hydrocarbon mixture is then transferred to the second method step (oligomerization), where the oligomerization takes place at temperatures preferably between 200 and 450° C. and at a pressure of 40 to 100 bar, likewise in the presence of pentasil-type zeolite catalysts. The olefins produced by oligomerization predominantly contain greater than 5, preferably 10 to 20, carbon atoms. The resulting mixture is worked up in a subsequent separation process, in which a distillate is separated which after hydrogenation of the main product forms diesel fuel. In addition, two hydrocarbon streams of different compositions are prepared, of which stream 3 is recirculated to the first method step and stream 4 is recirculated to the second method step. It is particularly advantageous when the molar ratio of steam in the recycle stream 3 [sic; 2] to the oxygenates in the feed stream 1 is between 0.1 and 5.

Finally, the by-products gasoline, LPG, and heating gas are separated.

For experimental verification of the increase in the olefin yield by use of the method according to the invention, a $C_5$ olefin stream was metered into the feed stream for the olefin reactor composed of methanol, dimethyl ether, and water according to the prior art. The resulting quantities of propylene, total olefins, paraffins, naphthenes, and aromatics in the obtained product were determined.

For comparison, the gas composition of the resulting product stream was determined for the method according to the invention, using a substantially inert paraffin carrier gas in the first method step. Also in this operating mode for the olefin reactor, the quantity of obtained propylene and total olefins as well as the quantity of resulting paraffins, naphthenes, and aromatics was determined. The results are provided in Table 1 below, in which the hydrocarbon yield is expressed relative to 100 parts carbon in the methanol used.

TABLE 1

|  | Poly-propylene | Olefin | Paraffin | Naphthene | Aromatics | Other |
|---|---|---|---|---|---|---|
| Olefin recycling | 63.1 | 65.1 | 18.2 | 2.5 | 10.3 | 3.9 |
| Inventive method | 37.9 | 80.7 | 10.6 | 0.7 | 5.1 | 2.9 |

The yields in the table were calculated by subtracting the moles of the recirculated olefin stream and of the recirculated paraffin carrier gas from both the reactor feed and the reactor product, since these are internal recirculation streams relative to the overall method.

The table shows the methanol conversion with and without recirculation of olefins. It is clearly seen that performing recirculation optimizes the propylene yield. On the other hand, in the method according to the invention the quantity of propylene is reduced, but the overall yield of 80.7 for olefins is particularly high.

In contrast to the prior art, in the method according to the invention the preferred recirculation of paraffins and of water results in a change in the reaction conditions in the fixed-bed reactor of the first method step with regard to temperature profile and partial pressure of the reactive components, such that more reactive olefins enter the oligomerization reactor, thereby greatly increasing the yield of diesel fuel.

The process steps of olefin production and oligomerization were investigated for over 10,000 hours in laboratory and pilot plant tests under various operating conditions. Evaluation of these tests allowed process simulation of the three method steps of olefin production, oligomerization, and separation.

The invention claimed is:

1. A method for producing a synthetic fuel from a gas mixture comprising an oxygenate wherein the oxygenate is methanol and/or dimethyl ether and/or another oxygenate, which comprises the steps of:
    (a) heating the gas mixture comprising an oxygenate wherein the oxygenate is methanol and/or dimethyl ether and/or another oxygenate, to a temperature of 300 to 600° C. in the presence of steam to produce olefins having 2 to 8 carbon atoms and saturated hydrocarbons;
    (b) separating the olefins having 2 to 8 carbon atoms from the saturated hydrocarbons formed during step (a) and the steam, and recycling the saturated hydrocarbons and the steam back to the beginning of step (a);
    (c) oligomerizing the olefins having 2 to 8 carbon atoms at elevated pressure to form higher olefins having 10 to 20 carbon atoms resulting in a reaction mixture of the higher olefins, olefins having 2 to 8 carbon atoms, and a gas stream of saturated hydrocarbons;
    (d) separating the olefins having 2 to 8 carbon atoms from the reaction mixture in step (c) and recycling the olefins having 2 to 8 carbon atoms back to the beginning of step (c)
    (e) separating the saturated hydrocarbons from the reaction mixture in step (c) and forming a gas stream combining the saturated hydrocarbons from the reaction mixture in step (c) with the saturated hydrocarbons recycled from step (b) back to the beginning of step (a);
    (f) hydrogenating the higher olefins having 10 to 20 carbon atoms obtained according to step (c) to obtain diesel fuel and by-products selected from the group consisting of gasoline, liquefied petroleum gas and heating gas; and
    (g) separating the by-products formed according to step (f) from the diesel fuel.

2. The method for producing a synthetic fuel defined in claim 1 wherein the oxygenate is methanol, dimethyl ether or a mixture of methanol and dimethyl ether.

3. The method for producing a synthetic fuel defined in claim 1 wherein a pentasil-type zeolite catalyst or catalysts based on silicalite or aluminum phosphate (SAPO type) are used for both the olefin production according to step (a) and the oligomerization according to step (c).

4. The method according to claim 3 wherein a pentasil-type, proton-containing catalyst having an Si/Al atomic ratio of greater than 10, a BET surface of 300 to 600 m$^{2}$/g, and a pore volume of 0.3 to 0.8 cm$^{3}$/g determined by mercury porosimetry is used as zeolite catalyst.

5. The method according to claim 1 wherein according to step (c) the oligomerization is carried out at a temperature of 200 to 450° C. and a pressure of 40 to 100 bar.

6. The method according to claim 1 wherein the olefin-production according to step (a) and the oligomerization according to step (c) are carried out in one or more adiabatic fixed-bed reactors having one or more stages, parallel or in series.

7. The method according to claim 1 wherein according to step (a) the molar ratio of the saturated hydrocarbons, recycled from step (e), to the oxygenates is between 0.5 and 10.

8. The method according to claim 1 wherein according to step (e) the combined gas stream re-circulated to step (a) is composed predominantly of saturated $C_2$ to $C_9$ hydrocarbons.

9. The method according to claim 1 wherein according to step (a) the molar ratio of the steam, recycled from step (b), to the oxygenate in the gas mixture is between 0.1 and 5.

10. The method according to claim 1 wherein the composition of the saturated hydrocarbons, produced according to step (c) differs from that of the composition of the saturated hydrocarbons, produced according to step (a).

* * * * *

UNITED STATES PATENT AND TRADEMARK OFFICE
CERTIFICATE OF CORRECTION

| | | |
|---|---|---|
| PATENT NO. | : 7,655,825 B2 | Page 1 of 1 |
| APPLICATION NO. | : 11/795930 | |
| DATED | : February 2, 2010 | |
| INVENTOR(S) | : Martin Rothämel et al. | |

It is certified that error appears in the above-identified patent and that said Letters Patent is hereby corrected as shown below:

Title Page, Item (75)

The correct spelling of the fourth (4th) inventor's first name should be shown as:

-- Harald -- Koempel (H a r a l d  K o e m p e l)

Signed and Sealed this

Twenty-third Day of March, 2010

David J. Kappos
*Director of the United States Patent and Trademark Office*